United States Patent [19]

Said

[11] 4,119,618

[45] Oct. 10, 1978

[54] VASOACTIVE POLYPEPTIDE AND METHOD OF PREPARATION FROM NEURAL TISSUE

[76] Inventor: Sami I. Said, 5323 Harry Hines Blvd., Dallas, Tex. 75235

[21] Appl. No.: 681,045

[22] Filed: Apr. 28, 1976

[51] Int. Cl.$^2$ .................. C07C 103/52; C07G 7/00
[52] U.S. Cl. .................. 260/112 R; 260/112.5 R; 424/95; 424/177
[58] Field of Search .................. 260/112 R; 424/177, 424/95

[56] References Cited

U.S. PATENT DOCUMENTS

| 2,162,863 | 6/1939 | Ripke et al. | 424/75 |
|---|---|---|---|
| 3,879,371 | 4/1975 | Said et al. | 424/177 |
| 3,898,329 | 8/1975 | Said et al. | 124/177 |

OTHER PUBLICATIONS

Protides of the Biological Fluids, Peeters, 1966, pp. 211–216 (Quamina et al.).
Handbook of Neurochemistry, vol. 1, 1969, Bogoch, pp. 75–92.

*Primary Examiner*—Howard E. Schain
*Attorney, Agent, or Firm*—Lowe, King, Price & Becker

[57] ABSTRACT

A new polypeptide of unknown composition has been extracted from neural tissue and detected in central nervous system and sympathetic ganglia, which new polypeptide exhibits vasoactive activity in various biological areas such as bronchodilation since the peptide is a smooth muscle relaxant.

9 Claims, No Drawings

VASOACTIVE POLYPEPTIDE AND METHOD OF PREPARATION FROM NEURAL TISSUE

ORIGIN OF THE INVENTION

The invention described herein was made in the course of work conducted under a grant or award from the United States Department of Health, Education and Welfare.

BACKGROUND OF THE INVENTION

1. Field of the Invention

This invention relates to a new polypeptide of unknown structure which exhibits biological activity, including vasoactivity, said polypeptide having been found in and extracted from neural tissue.

2. Description of the Prior Art

It is well known that polypeptide hormones regulate many physiologic functions and mediate certain pathological responses. While numerous compounds have been known to possess a vasodilator effect, many possess this effect only to a relatively slight degree or for a very short time. Medical science has therefore sought materials exhibiting a more potent or sustained vasodilator effect and which would be more useful therapeutic agents.

In prior U.S. Pat. Nos. 3,879,371; 3,880,826; 3,862,927 and 3,898,329, there is disclosed a new polypeptide indentified as a Vasoactive Intestinal Peptide which polypeptide is a 28 residue peptide structurally and biologically related to secretin and glucagon. The VIP polypeptide was originally isolated from porcine duodenum and was found throughout the gastrointestinal tract of mammals and birds. This polypeptide exhibited a wide variety of therapeutic biological actions including systemic vasodilation, hypotension, increased cardiac output, respiratory stimulation, hyperglycemia, coronary dilation and bronchodilation in animals and humans.

The present invention provides a new polypeptide of unknown structure which has been extracted from neural tissue and has been detected as being present in other tissue. The polypeptide of this invention is related to the vasoactive intestinal peptide of these prior patents and may exhibit similar therapeutic actions.

SUMMARY OF THE INVENTION

It is accordingly one object of this invention to provide a new polypeptide which exhibits important biological actions.

It is a further object of this invention to provide a new polypeptide of unknown structure which exhibits broad biological activity including relaxation of smooth muscle. As it is vasoactive, it may also be useful in the areas of systemic vasodilation, hypotension, cardiac output increase, respiratory stimulation, coronary dilation and bronchodilation in animals and humans.

A further object of this invention is to provide methods for the isolation of this new vasoactive polypeptide from neural tissue.

Other objects and advantages of the present invention will become apparent as the description thereof proceeds.

In satisfaction of the foregoing objects and advantages there is provided by this invention a new polypeptide of unknown structure which exhibits vasoactive characteristics, which new polypeptide has been extracted from tissues of mammals of neural origin such as nervous tissues. The method of extraction comprises obtaining samples of normal neural tissue, extracting with dilute organic acid or mixtures of acid and a lower alkyl alcohol, concentrating the extracts by adsorption to alginic acid, eluting with HCl and salting out or precipitating. The product is then subjected to the separation and recovery steps described in U.S. Pat. No. 3,879,371 by which the Vasoactive Intestinal Peptide is recovered and the disclosure of that prior patent is incorporated herein by reference.

DESCRIPTION OF PREFERRED EMBODIMENTS

According to the present invention there has been discovered a new polypeptide which exhibits vasoactive characteristics similar to the vasoactive intestinal polypeptide described in the prior patents mentioned above. The new polypeptide of this invention was discovered in a search for similar polypeptides in cloned tumor cell lines of neural origin and in normal nervous tissues.

According to the present invention this polypeptide has been extracted from neural tissue by a process generally comprising the steps of obtaining samples of neural tissue from test animals, extracting the tissue with an organic carboxylic acid, or mixture of organic carboxylic acid and lower alkyl alcohol, concentrating the peptides from the extracts by adsorption to alginic acid, eluting with HCl and recovering the product by salting out or precipitation with ether.

In our study of the neural vasoactive polypeptide of this invention it was determined that this material was distributed throughout various tissues of test animals. Thus, it was found that the peptide was present in high levels of immuno-assayable peptide in clonal neuroblastoma and astrocytoma cell lines, of neuronal and glial origin, respectively. The peptide or a peptide that cross-reacts with it, was also present in normal brain tissue, with the highest concentrations in cerebral cortex, and the lowest in cerebellum and brainstem.

In extraction of the peptide, samples of normal neural tissue were taken from different parts of the brain, peripheral sympathetic chain and vagus nerve. These samples were removed from dogs within one hour after exsanguination, and were extracted in dilute acetic acid or a mixture (50/50) of acetic and ethyl alcohol. The peptides were concentrated from these extracts by adsorption to alginic acid, followed by elution with 0.2 M HCl and salting out or by precipitation with ether.

The resulting mixture is then subjected to the steps of isolation as described for the Vasoactive Intestinal Peptide of U.S. Pat. No. 3,879,371. Thus, the mixture is initially subjected to gel chromatography over Sephadex. Thereafter, the recovered active fraction is subjected to two consecutive separations by ion-exchange chromatography. The ion-exchange chromatography steps are conducted in a carboxymethylcellulose column. The active fraction obtained from the second ion-exchange chromatography step is then subjected to countercurrent distribution and the product recovered by lyophilization. All of these separation and purification steps are fully described in U.S. Pat. No. 3,879,371, the disclosure thereof being expressly incorporated herein by reference.

The immunoreactivity of the peptide was measured by a highly specific radioimmunoassay which has been improved to detect 50 pg per ml of the peptide. All samples were assayed in duplicate, and the assay was performed at least twice. In this assay, peptide antibodies showed minimal (<1:1000) or no cross-reaction with secretin (GIH Laboratory, Karolinska Institute, Stockholm), glucagon (Eli Lilly), cholecystokinin-pancreozymin (GIH Laboratory), bradykinin (synthetic, Sandoz), substance P (synthetic bovine, Beckman) or somatostatin (synthetic ovine, Beckman).

The immunoreactivity of the peptide was determined as follows: neuroblastoma cell lines, derived from transplantable, C 1300 mouse neuroblastoma, comprised three clones: NE115, which is adrenergic, S20 which is cholinergic; and C46 which is neither adrenergic nor cholinergic (gifts of Dr. Marshall W. Nirenberg, National Institutes of Health, Bethesda, Maryland). The glial cell line was the C6 rat astrocytoma clone. Cell monolayers were grown in Dulbecco's Modified Eagle's Medium, containing 10 percent fetal calf serum plus 200 μg per ml of spectinomycin. Cultures were grown in Falcon flasks or tissue culture dishes at 37° C. in an atmosphere of 10 percent $CO_2$ in air, at 100 percent humidity. Cells from exponentially growing cultures of each line were inoculated into a series of 100mm tissue culture dishes. At specified intervals, one plate from each line was scraped off and the cells were counted (Coulter counter), suspended in 2 ml of buffer (0.05 M $KH_2PO_4$, 0.001 M EDTA, adjusted to pH 7.3 with KOH), and sonicated before assay of the peptide.

Cells from all three neuroblastoma lines were rich in the peptide as shown in the following Table 1, with a concentration ranging from 0.6 ng per million cells (or 2.2 ng per mg protein) to 0.9 ng per million cells (or 3.6 ng per mg protein). In each case, as the cell counts increased between the second and fifth days, total peptide levels also increased, though the concentration per million cells decreased. Astrocytoma cells were also rich in the peptide but the peptide concentration in these cells was less than half that in neuroblastoma cells. The buffer solution in which cells were suspended, and the medium in which they were grown, contained nondetectable levels of the peptide. After incubation for at least one day, however, immunoassayable peptide was demonstrable in cell-free medium, in concentrations of approximately 200 pg per ml.

Peptide immunoreactivity was also present in normal neural tissue as shown in the following Table II, being highest in cortex from frontal and white matter from frontal lobe, and lowest in cerebellum, brain stem and vagus nerve. Peptide concentrations per g wet weight were lower in duodenum, ileum and colon than in the richest nervous tissues, raising the possibility that the peptide content in gastrointestinal organs may be partly due to the innervation of these organs. Skeletal muscle and liver contained traces or nondetectable levels of the peptide. This distribution of peptide resembles in some respects (e.g., its paucity in cerebellum and liver) the tissue distribution of norepinephrine.

TABLE II

Distribution of peptide immunoreactivity in brain, gastrointestinal, and other tissues.

| Tissue | Peptide (ng per g wet weight) |
|---|---|
| A) Nervous Tissues: | |
| Frontal lobe cortex | 61 |
| Frontal lobe white matter | 35 |
| Temporal lobe cortex | 24 |
| Occipital cortex | 66 |
| Cerebellar cortex | 2 |
| Hippocampus | 39 |
| Thalamus | 2 |
| Hypothalamus | 65 |
| Pons | 1.3 |
| Medulla | 2.5 |
| Midbrain | 3.3 |
| Sympathetic nerve | 6.4 |
| Vagus | 0.6 |
| B) Gastrointestinal Tissues: | |
| Duodenum | 13.2 |
| Ileum | 14.0 |
| Ascending colon | 10.6 |
| Liver | <0.06 |
| C) Ohther Tissues: | |
| Skeletal muscle | 0.1 |

Extracts of frontal lobe cortex and of neuroblastoma cells (C45 clone) were assayed for peptide-like biological activity, based on their ability to relax isolated, superfused rat stomach strip and guinea pig gallbladder. The bioassay confirmed the presence of biologically active peptide. The high levels of peptide in both gray and white brain matter correlates with its presence in tumor cell lines of both neuronal and glial origin. These findings, and the selective distribution of the peptide in the central and autonomic nervous systems, suggest a possible function for this peptide, or one that is similar to it, in the nervous system. Until additional data are available, including the possible effects of the peptide on neural function, its physiologic role remains speculative. Such a role could include a modulator, trophic, growth-promoting, or transmitter action. An endothelial proliferative factor, elaborated by clonal cell lines of neural origin is probably distinct from the peptide, since this factor is reported to be destroyed by heating to 56° C. for 10 minutes, while the peptide resists boiling for that period.

TABLE I

| | Peptide concentrations in neuroblastoma and astrocytoma cell cultures. | | | | | | | |
|---|---|---|---|---|---|---|---|---|
| | Neuroblastoma | | | | | | Astrocytoma | |
| Days from inoculation | Clone NE 115 | | Clone S20 | | Clone C46 | | Clone C6 | |
| | Cells | Peptide | Cells | Peptide | Cells | Peptide | Cells | Peptide |
| | ($\times 10^6$/plate) | (ng/plate) | ($\times 10^6$/plate) | (ng/plate) | ($\times 10^6$/plate) | (ng/plate) | ($\times 10^6$/plate) | (ng/plate) |
| 2 | 5.5 | 6.2 | 4.5 | 5.8 | 4.9 | 5.7 | | |
| 5 | 27.4 | 16.0 | 15.6 | 13.2 | 26.6 | 17.4 | 30 | 6.5 |

The polypeptide of this invention exhibits generally similar biological characteristics to the Vasoactive Intestinal Peptide described in the prior patents mentioned above. It has been determined to have smooth muscle relaxant activity and thus is useful as a bronchodilator and for gastrointestinal pain. However, because of its vasodilation characteristics, its biological activity may also include systemic vasodilation, hypotension, increased cardiac output, respiratory stimulation, hyperglycemia, and bronchodilation, in humans and animals. It may be administered as described for the Vasoactive Intestinal Peptide described in the above-mentioned patents.

The following example is presented to illustrate the invention but is not to be considered as limited thereto.

In the following example parts are by weight unless otherwise indicated.

EXAMPLE

Samples of normal neural tissue were obtained from 5 different parts of the brain, peripheral sympathetic chain and vagus nerve of dogs as test animals. The samples were removed from the dogs within one hour after exsanguination. The samples were then extracted with dilute acetic acid or a mixture of ethyl alcohol. The resulting extracts were then concentrated by adsorption to alginic acid. This step was conducted by dilution of the extract with alginic acid which had been prewashed with 0.2 N HCl and then with water. After stirring for one hour at room temperature, the alginic acid containing the absorbed peptide was collected on a suction filter with 0.005 N HCl. The filtrate and washings were discarded. The peptide was then eluted from the alginic acid by stirring for 10 minutes with 0.2 M HCl and salting out. The recovered peptide was then subjected to a gel chromatography separation over Sephadex G-25, two consecutive ion-exchange separations over CMC and the recovered active fraction subjected to countercurrent distribution. On lyophilization the active fraction was recovered and assayed as described above.

The invention has been described herein by reference to certain preferred embodiments. However, as obvious variations thereon will become apparent to those skilled in the art, the invention is not to be considered as limited thereto.

What is claimed is:

1. A process for the isolation of a new biologically active polypeptide from the neural tissue of mammals which consists essentially of the sequential steps of:
   (a) obtaining neural tissue;
   (b) extracting said neural tissue by contacting with a member selected from the group consisting of dilute organic acyclic carboxylic acids and mixtures of organic acyclic carboxylic acids with lower alkyl alcohols;
   (c) concentrating the resultant extract by contacting with alginic acid, filtering the resultant alginic acid containing the absorbed extract, and collecting the alginic acid containing the absorbed extract on the filter;
   (d) eluting the alginic acid containing the absorbed extract by contacting with HCl aqueous solution and recovering the extract from the HCl solution;
   (e) subjecting the resultant extract to gel chromatography in a chromatographic column and recovering the active fraction;
   (f) subjecting the resulting active fraction from step (e) to at least two consecutive ion exchange chromatographic steps in a chromatographic column and recovering the active fraction therefrom;
   (g) subjecting the active fractions to countercurrent distribution; and
   (h) subjecting the resultant active fraction to lyophilization and recovering the active fraction containing the polypeptide.

2. A process according to claim 1 wherein the neural tissue comprises parts of the mammal brain, peripheral sympathetic chain, and vagus nerve.

3. A process according to claim 2 wherein the neural tissue is obtained within one hour of exsanguination.

4. A process according to claim 1 wherein the organic carboxylic acid is acetic acid.

5. A process according to claim 1 wherein elution in step (d) is conducted with 0.2 M HCl solution.

6. A process according to claim 5 wherein the active fraction is recovered from the elution step (d) by salting out of the HCl solution.

7. A process according to claim 5 wherein the peptide is recovered from elution step (d) by precipitation with ethyl ether from the HCl solution.

8. A process according to claim 1 wherein ion-exchange chromatographic step (f) is conducted in a chromatographic column containing a cross-linked dextran.

9. A process according to claim 1 wherein the gel chromatographic step (e) conducted in a chromatographic column containing carboxymethylcellulose.

* * * * *